United States Patent [19]

Ziegler et al.

[11] Patent Number: 5,488,106
[45] Date of Patent: Jan. 30, 1996

[54] PROCESS FOR PREPARING 6-[(ISOXAZOLINYL)METHYL]PENICILLANIC ACID 1,1-DIOXIDE COMPOUNDS

[75] Inventors: Carl Ziegler; Paul Fabio, both of Pearl River, N.Y.; Karen Bush, Kingston, N.J.; Deborah Steinberg, Pomona, N.Y.

[73] Assignee: American Cyanamid Company, Wayne, N.J.

[21] Appl. No.: 193,496

[22] Filed: Feb. 7, 1994

[51] Int. Cl.$^6$ .................. C07D 499/00; A61K 31/43
[52] U.S. Cl. .................................................. 540/310
[58] Field of Search ................... 540/310; 514/210, 514/192, 193, 195

[56] References Cited

U.S. PATENT DOCUMENTS 5,015,473  5/1991  Chen .......................... 424/114

FOREIGN PATENT DOCUMENTS 2206579  1/1989  United Kingdom .

OTHER PUBLICATIONS

T. Greene, Protective Groups in Organic Synthesis, J. Wiley & Sons, 1981, pp. 53–61.
Volkmann et al., J. Org. Chem., vol. 47, pp. 33–44 (1982).
Hannessian, Tetrahedron, vol. 45, pp. 941–950 (1989).
N. A. Kuck, et al., "Antibiotic Agents and Chemotherapy", vol. 33, 1989, pp. 1964–1969.
A. Brandi et al., J. Org. Chem., vol. 54, pp. 3073–3077 (1989).
Mukaiyama et al., J. Am. Chem. Soc., vol. 82, pp. 5339–5345 (1960).
Weeks and Volkmann, Tetrahedron Letters, vol. 27, pp. 1549–1552 (1986).
L. A. Reed et al., Tetrahedron Letters, vol. 28, 3431–3434 (1987).
Hannessian et al., Tetrahedron Letters, vol. 27, pp. 4857–4860 (1986).
Kou-Chang Liu et al., J. Org. Chem., vol. 45, pp. 3916–3918 (1980).
Just et al., J. Org. Chem., 52, 36–59 (1987).
Foulds et al., J. Chem. Soc. Perkin Trans I, 963–968 (1985).
D. M. Vyas et al., Tetrahedron Letters, 25, 487–490 (1984).
H. C. New, "Antibiotic Inhibitors of Bacterial Cell Wall Biosynthesis", D. J. Tipper ed, Pergamon Press, 1987, 241–259.
K. Bush, "Antibiotic Agents and Chemotherapy", vol. 33, 1989, pp. 259–276.
Yang et al., "Antibiotic Agents and Chemotherapy", vol. 36, 1992, 1155–1157.

*Primary Examiner*—Nicholas Rizzo
*Attorney, Agent, or Firm*—T. S. Szatkowski

[57] ABSTRACT

The invention provides a novel class of 6-(isoxazolinyl)methyl penicillanic acid 1,1-dioxide compounds having the formula:

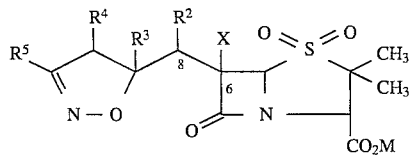

wherein M, X, $R^2$, $R^3$, $R^4$ and $R^5$ are described in the specification;
which exhibit activity as a β-lactamase inhibitor.

2 Claims, No Drawings

PROCESS FOR PREPARING 6-[(ISOXAZOLINYL)METHYL] PENICILLANIC ACID 1,1-DIOXIDE COMPOUNDS

BACKGROUND OF THE INVENTION

1. Field of the Invention

The invention relates to novel 6-(isoxazolinyl)methyl] penicillanic acid 1,1-dioxide compounds having activity as β-lactamase inhibitors.

SUMMARY OF THE INVENTION

The invention provides novel 6-(isoxazolinyl)methyl] penicillanic acid 1,1 dioxide compounds having the formula:

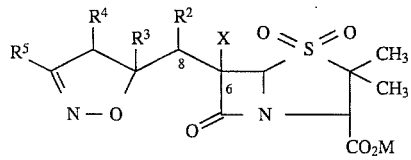

wherein:

M is H, Na, Li or K;

X is OH or Br;

$R^2$ is H; $C_1$–$C_4$ alkyl; —OCOCH$_3$; OH; —OCOC$_6$H$_5$; $C_1$–$C_4$ substituted alkyl with substitution selected from F, Cl, Br, I, OH and NH$_2$; acetate; NH$_2$; benzoate; F; Cl; Br; or I;

$R^3$ is H; $C_1$–$C_4$ alkyl; $C_1$–$C_4$ substituted alkyl with substitution selected from F, Cl, Br, I, OH and NH$_2$; acetate; NH$_2$; OH; benzoate; F; Cl; Br; or I;

$R^4$ is H; $C_1$–$C_4$ alkyl; $C_1$–$C_4$ substituted alkyl with substitution selected from F, Cl, Br, I, OH and NH$_2$; acetate; NH$_2$; OH; benzoate; F, Cl, Br or I;

$R^5$ is H; $C_1$–$C_4$ alkyl; $C_1$–$C_4$ substituted alkyl with substitution selected from F, Cl, Br, I, OH, and NH$_2$; 2- or 3-thienyl; F; Cl; Br; I; phenyl; or substituted phenyl with substitution selected from $C_1$–$C_4$ alkyl, F, Cl, Br, I, OH, or NH$_2$; which compounds exhibit activity as β-lactamases inhibitors and more particularly as inhibitors of group 3 metallo β-lactamases. The invention also provides novel intermediate compounds, a novel method of making the 6[(isoxazolinyl)methyl]penicillanic acid 1,1-dioxide compounds of the present invention, a method of using the novel compounds of the present invention to inhibit β-lactamases and a pharmaceutical composition containing the novel compounds of the present invention.

DESCRIPTION OF THE PREFERRED EMBODIMENTS

The novel 6-[(isoxazolinyl)methyl]penicillanic acid 1,1-dioxide compounds of the present invention are prepared according to the following reaction schemes:

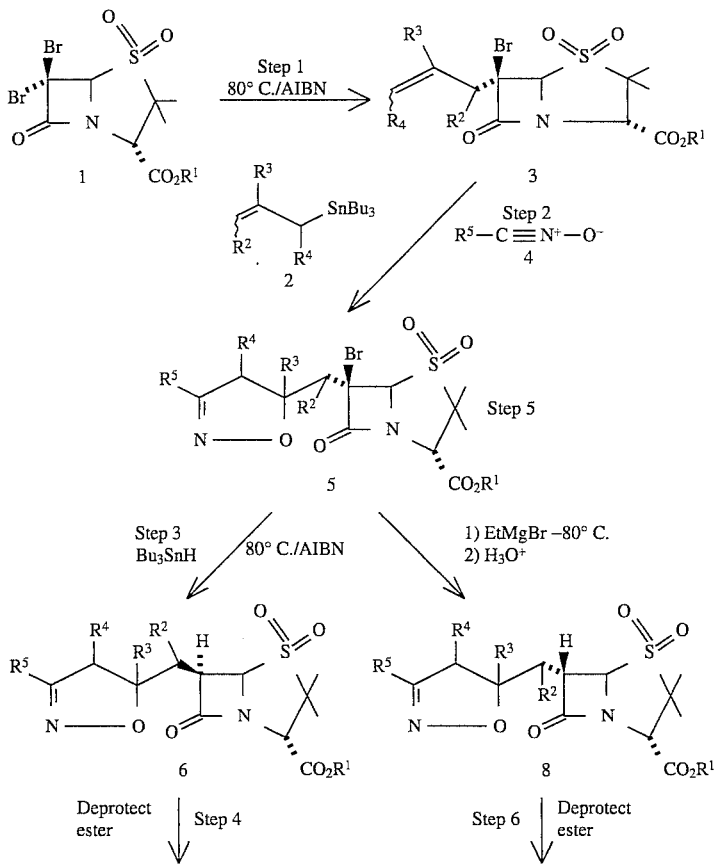

Scheme 1

Scheme 1
-continued

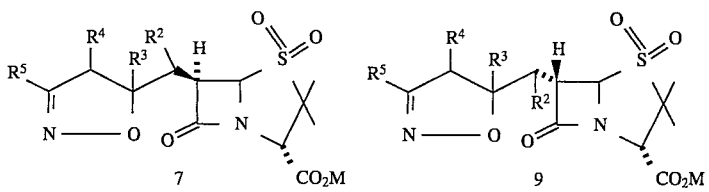

Referring to Scheme 1, 6,6-dibromopenicillanate 1,1-dioxide, 1, where $R^1$ is an acid protecting group, is prepared by the method of Volkmann et al, *J. Org. Chem.*, Vol. 47, p.3344 (1982). For 6,6-dibromopenicillanate 1,1-dioxide, 1, preferred substituents for $R^1$ include $C_1$–$C_4$ alkyl, halogen substituted $C_1$–$C_4$ alkyl, $C_1$–$C_4$ alkyloxymethyl, $C_1$–$C_4$ acyloxy methyl, 1-($C_1$–$C_4$ alkoxy)carbonyloxy ethyl, p-nitrobenzyl, benzyl and allyl. Contemplated equivalents include any substituent which functions as an acid protecting group.

In Step 1 of Scheme 1, 6β-bromo-6-α-(substituted allyl-)penicillanate 1,1 dioxide, 3, is formed on contacting 6,6-dibromopenicillanate 1,1-dioxide, 1, with allyltributylstannane, 2, in the presence of azobisisobutyronitrile (AIBN) at 80° C. similarly to the method reported by Hannessian, *Tetrahedron*, Vol. 45, pp 941–950 (1989) wherein $R^2$–$R^4$ are as defined hereinbefore except that for this reaction scheme, $R^2$ cannot be OH, acetate, benzoate or amino.

In Step 2 of Scheme 1, a [3+2] dipolar cycloaddition of nitrile oxide, 4, wherein $R^5$ is as defined hereinbefore, with penicillanate 1,1-dioxide, 3, yields the cycloadduct 6-[(isoxazolinyl)methyl]penicillanate 1,1-dioxide, 5, wherein $R^1$ and $R^2$–$R^5$ are as hereinabove defined. The reaction in Step 2 is usually initiated at low temperatures such as, but not limited to −78°, in an inert solvent such as but not limited to toluene or methylene chloride. The reaction temperature usually is allowed to gradually warm to ambient temperature (25° C.) over a period of 0.5–5 hours with one hour being preferred. The nitrile oxide, 4, is obtained via the method of A. Brandi, et.al. *J. Org Chem. Vol.* 54, pp 3073–3077, 1989 (from the corresponding imidoyl chloride) or the method of Mukaiyama et al. *J. Am. Chem. Soc.*, Vol. 82, pp 5339–5345, 1960 (from nitro parrafins).

In Step 2, the reaction produces adequate yields of product 5, when 1 equivalent of allyl penicillanate 3 and 1.2 equivalents of nitrile oxide 4 are used. Reaction concentrations usually are maintained in the range of 0.2 to 0.8 molar for the limiting allyl penicillanate 3. The reaction product 5 is isolated following conventional techniques in the art including filtration, washing, crystallization, chromatography and the like. Yields of product 5 are in the range of 30 to 85%. The product consists of a mixture of diastereomers. For instance, in the simplest case where $R^2$, $R^3$, $R^4$=H, allylpenicillanate 3 reacts with nitrile oxide 4 to give 5 which is a mixture of 2 diastereomers. In the product 5 mixture the newly formed asymmetric carbon bearing $R^3$ has the R-absolute stereochemistry in one isomer and the S-absolute configuration in the other isomer. The ratio of R to S in this case is close to unity.

In Step 3 of Scheme 1, the 6β-bromopenicillate 1,1-dioxide 5 is reduced by contacting it with tributyltin hydride in the presence of a catalytic amount of azoisobutyronitrile (AIBN) in benzene solvent usually at elevated temperatures ranging from ambient to 80° C. The isolation of product 6 follows conventional techniques in the art including filtration, washing, crystallization, chromatography and the like. Yields of product 6 are in the 60–90% range. The product 6 reflects reduction from the α face to form the 6β-[ (substituted isoxazolinyl)methyl]penicillanate 1,1-dioxide 6, wherein $R^1$, $R^2$, and $R^5$ are as hereinabove described. The reduction in Step 3 Scheme 1 follows the procedure of Hanessian, *Tetrahedron*, Vol. 45, pp 941–950 (1989).

In Step 4 of Scheme 1, the acid protecting group $R^1$ of 6 may be removed to give the corresponding product 7 by conventional procedures such as solvolysis, chemical reduction or hydrogenation. Where a protecting group such as p-nitrobenzyl or benzyl is used catalytic hydrogenation in a suitable solvent system can be used. Suitable solvent systems include ethyl acetate-water-sodium bicarbonate, dioxane-water-ethanol, tetrahydrofuran-diethylether-buffer, tetrahydrofuranaqueous dipotassium hydrogen phosphate-isopropanol or the like. Compound 6 may be treated under a hydrogen pressure of from 1 to 4 atmospheres in the presence of a hydrogenation catalyst such as palladium on charcoal, palladium hydroxide, platinum oxide or the like at temperatures ranging from 0° to 40° C. for 0.2 to 4 hours. Protecting groups such as 2,2,2-trichloroethyl may be removed by mild zinc reduction. The allyl protecting group may be removed by using a catalyst comprising a mixture of a palladium compound and triphenylphosphine in a suitable aprotic solvent such as tetrahydrofuran, methylene chloride or diethyl ether. Similarly, other conventional carboxyl acid protecting groups may be removed by methods known to those skilled in the art.

Compounds of formula 6 where $R^1$ is a physiologically hydrolyzable ester such as acetoxymethyl, pivaloyloxymethyl, etc., may be administered directly to the host without deblocking since such esters are hydrolyzed in vivo under physiological conditions. Depending on the carboxyl protecting group, the method of deprotection, as described above, will vary. Product isolation from the deprotection step again varies based on the method used, but all methods used in this transformation follow conventional techniques in the art including chromatography and lyophilization.

A variation within Scheme 1 allows the preparation of 6α-[(substituted isoxazolinyl)methyl] penicillanate 1,1-dioxide 8. Thus, in Step 5 of Scheme 1, a compound of formula 5 is reduced, with stereochemical retention, from the β-face of the molecule to give compound of formula 8 where $R^1$, $R^2$ and $R^5$ are as hereinabove defined. Reduction is achieved in Step 5 by contacting the 6β-bromopenicillanate 5 with a suitable alkylorganometallic reagent such as ethylmagnesium bromide in a suitable solvent such as tetrahydrofuran at low temperatures such as −70° C. and under an inert atmosphere such as argon or nitrogen. The intermediate metallated penicillanate species thus formed is subsequently contacted with a weak acid such as aqueous 1 molar acetic acid solution followed by warming to ambient temperatures. The product isolation follows conventional techniques in the art including filtration, washing, crystallization, chromatography and the like. Yields of 8 are in the range of 50–90%. The reaction in Step 5 of Scheme 1 with its procedure, choice of reaction conditions and stereochemical outcome is precedented for other non-related 6β-bromo-6α-alkylpenicillanate substrates. The procedure of Weeks and Volkmann is illustrative; *Tetrahedron Letters,* Vol 27, pp 1549–1552 (1986).

In Step 6 of Scheme 1, the carboxyl protecting group $R^1$ of compound 8 may be removed as was described previously in Step 4 of Scheme 1. The corresponding carboxylate salt of formula 9 so obtained differs from the carboxylate salt 7 from Step 4 of Scheme 1 by the α-orientation of its 6-[(substituted isoxazolinyl)methyl] moiety (relative to the 6-β orientation for 7). Isolation and purification and yields of carboxylate salts of formula 9 are similar to those described for carboxylates 7 from Step 4 of Scheme 1.

carbons bearing the bromide (C-6) and that bearing the —OH moiety (C-8). The reaction in Step 1 of Scheme 2 is similar to that reported by L. A. Reed et al, *Tetrahedron Letters* Vol. 28, pp. 3431–3434 (1987).

In Step 2 of Scheme 2, the diastereomeric mixture of compounds of formula 11 is treated with tributyltin hydride at elevated temperatures such as 80° C. in an inert solvent such as toluene. The reaction type represented here in Step 2 as well as the procedure, workup and isolation of the product 12 is similar to that described for the preparation compound (in Step 3 of Scheme 1). In Step 2 of Scheme 2, the product 12 reflects reduction from the o-face which is exhibited by all other tin hydride/6-bromopenicillanate reductions of this type wherein $R^1$, $R^3$ and $R^4$ are hereinabove defined. Yields of product 12 range from 35–85%.

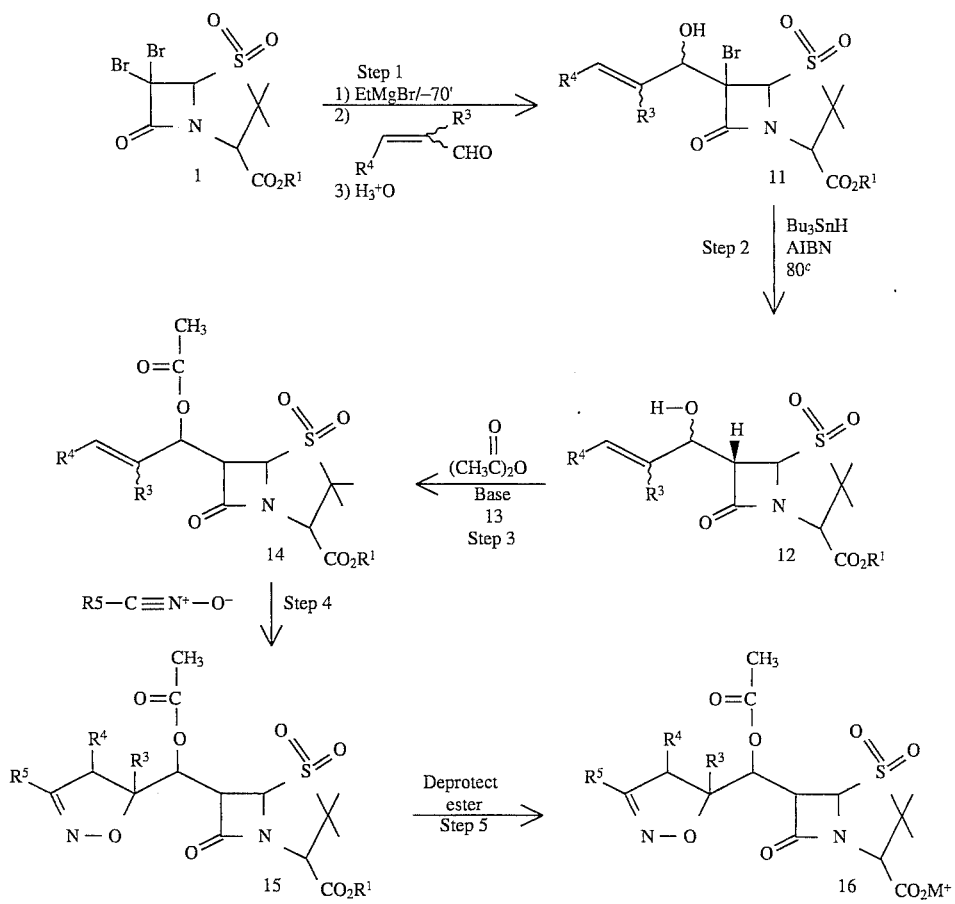

Scheme II

Referring next to Scheme 2, 6,6-dibromopenicillanate 1,1-dioxide 1 is sequentially treated with an alkylorganometallic reagent such as ethylmagnesium bromide at low reaction temperatures in an inert solvent such as tetrahydrofuran, diethylether or toluene. Following this, the metallated penicillanate is contacted with a suitable unsaturated aldehyde wherein $R^3$ and $R^4$ are as hereinabove defined. Subsequent to this, the reaction is quenched by the addition of a suitable acid such as acetic acid or an aqueous solution of potassium dihydrogen phosphate. The product 11 is isolated following conventional techniques in the art including filtration, washing, crystallization, chromatography and the like. Yields of product 11 are in the range of 30 to 70%. The product 11 consists of a mixture of diastereomers about the In Step 3 of Scheme 2, the allylic alcohol substituted penicillanate 1,1-dioxide of formula 12 is contacted with a suitable acylating agent and base in a suitable solvent to form the acylated penicillanate 14. Suitable acylating agents include acetic anhydride 13. Suitable solvents include pyridine, methylene chloride, diethylether, tetrahydrofuran or dimethylformamide. A variety of bases suitable for this transformation include pyridine, triethylamine and N,N-dimethylaminopyridine. These reactions are usually carried out under anhydrous conditions at temperatures ranging from −25° C. to +25° C. The product 14 is isolated via conventional techniques which include filtration, washing, crystallization, chromatography and the like. Yields of product 14 vary from 60% to 90%. This type of transformation is typified by Greene in "Protective Groups in Organic Synthesis" J. Wiley, 1981, pp 53–61.

In Step 4 of Scheme 2, a [3+2] dipolar cycloaddition of the nitrile oxide 4 with the 6-β (substituted allyl)penicillanate 1,1-dioxide 14 in a suitable solvent and at a suitable reaction temperature produces the cycloadduct β-[substituted isoxazolidinyl)methyl]penicillanate 1,1-dioxide 15. The transformation in Step 4 of Scheme 2 with its procedure, stoichiometry, reaction conditions, workup procedure and product isolation is similar to that hereinabove described in Step 2 of Scheme 1. Yields of product 15 are in the range of 25 to 70%.

In Step 5 of Scheme 2, the carboxyl protecting group $R^1$ of compound 15 may be removed to prepare the carboxylate salt of formula 16. The procedures, workup and product 16 isolation techniques available in Step 5 of Scheme 2 are the same as those described in detail in Steps 4 and 5 of Scheme 1. Product 16 yields vary from 10 to 50%.

It will be appreciated that the compounds of the present invention may exist as diastereomeric entities. It is intended that the present invention include within its scope all such diastereomers for positions 6 and 8 and for the carbons of the isoxazolinyl nucleus bearing the substituents $R^3$ and $R^4$. On the penam ring the R configuration is preferred for both positions 3 and 5.

The invention will be more fully described in conjunction with the following specific examples which are not to be construed as limiting the scope of the invention.

EXAMPLE 1

4-Thia-1-azabicyclo[3.2.0]heptane-2-carboxylic acid,
6-[[4,5-dihydro-3-(4-methylphenyl)-5-isoxazolyl]methyl]-
3,3-dimethyl-7-oxo-, diphenylmethyl ester,
4,4-dioxide, [ 2S-(2α, 5α, 6β)]-

The diphenylmethyl-6α-alkylpenicillanate used in this preparation is prepared by the method described by Hanessian and Alpegiani, *Tetrahedron Letters* Vol. 27 pp 4857–4860 (1986). The 4-tolylnitrile oxide is prepared in situ by the addition of triethylamine to a solution of N-hydroxytolyl 4-carboximidoylchloride prepared as described by Kou-Chang Liu et al *J. Org. Chem.* 45, pp 3916–18 (1980) in methylene chloride.

A solution of 200 mg (0.455 mmol) of 4-thia-1-azabicyclo [3.2.0]heptane-2-carboxylic acid, 3,3-dimethyl- 7-oxo-6-(2-propenyl)-, diphenylmethyl ester, 4,4-dioxide, [2S-(2α, 5α, 6α)] in 5 ml of methylene chloride is cooled under argon in an ice bath. A solution of the nitrile oxide is prepared from 77.2 mg. (0.455 mmol) of the imidoyl chloride and 46.1 mg (0.455 mmol) of triethylamine in 5 ml of methylene chloride. The cold solution of nitrile oxide is added with stirring to the cooled solution of α-allyl penicillanate. The reaction mixture is allowed to warm to room temperature. An additional 20% of nitrile oxide (15.5 mg) imidoyl chloride+9.2 mg triethylamine) is added. The reaction mixture is stirred for an additional hour at room temperature. The solvent is removed under reduced pressure to give 272 mg of crude product. Flash chromatography gives 208.5 mg (80%) of product, m.p. 80°–85° as a 1:1 mixture of diastereomers.

$^1$HNMR (CDCl$_3$) δ: 1.13 (d, 3H); 1.57 (d, 3H); 2.30 (m, 2H); 2.38(s,3H); 3.06(m, 1H); 3.50(m, 1H); 3.86(m, 1H); 4.47 (d, 1H); 4.73 (d, 1H), 4.90 (m, 1H); 7.40 (m, 14H) IR(neat): 1761 cm$^{-1}$; 1797 cm$^{-1}$ MS: FAB, 573 (M+H)$^+$.

EXAMPLE 2

4-Thia-1-azabicyclo[3.2.0]heptane-2-carboxylic acid, 6-[
[4,5-dihydro-3-(4-methylphenyl)-5-isoxazolyl]-methyl]
-3,3-dimethyl-7-oxo-, potassium salt, - 4,4-dioxide,
[2S-(2α,5α,6β)]-

A cooled solution, 0°, of the diphenylmethyl ester, prepared in Example 1, 101 mg(0.176 mmol)in 2 ml of methylene chloride is treated with 0.5 ml of trifluoroacetic acid. After 10 minutes at 0°, TLC still indicated the presence of starting ester. The reaction mixture is stripped of solvent under reduced pressure. The residual oil is cooled in an ice bath and is treated with 1 ml of trifluoroacetic acid. The reaction mixture is free of starting ester(TLC) after stirring at 0° for 30 minutes. The mixture is stripped of volatiles under reduced pressure and gives 107 mg of crude carboxylic acid. A solution of the acid in 1 ml of ethyl acetate is added to a solution of 37.5 mg (0.185 mmol) of potassium 2-ethyl hexanoate in 1 ml of ethyl acetate. A few drops of hexane is added and the mixture is cooled to −20° . The crystalline solid that forms is collected by filtration, washed with an ethyl acetate/hexane mixture and is dried under reduced pressure to give 34 mg of a white solid; m.p. 130°–135° (dec.) as a 1/1 mixture of diastereomers. $^1$HNMR (D$_2$O/TSP) δ: 1.45 (s, 3H); 1.57 (d, 3H); 2.32 (m, 2H); 2.39 (S, 3H); 3.52 (mm, 2H); 3.78 (mm, 1H); 4.21 (d, 1H); 4.98 (d, 1H); 5.07 (mm, 1H); 7.34 (d, 2H); 7.62 (t, 2H); MS:FAB, 445(M+H)$^+$. IR (KBr) 1626 cm$^{-1}$; 1784 cm$^{-1}$.

EXAMPLE 3A

4-Thia-1-azabicyclo[3.2.0]heptane-2-carboxylic acid, 6-[
[4,5-dihydro-3(4-methylphenyl)-5-isoxazolyl]methyl]-
3,3-dimethyl-7-oxo-, diphenylmethyl ester,
4,4-dioxide, [2S-(2α, 5α, 6β(R*)]-

EXAMPLE 3 B

4-Thia-1-azabicyclo[3,2,0]heptane-2-carboxylic acid, 6-[ [4,5
-dihydro-3(4-methylphenyl)-5-isoxazolyl]methyl]-
3,3-dimethyl-7-oxo-, diphenylmethyl ester,
4,4-dioxide, [2S-(2α,5α,6β(S*)]-

The diphenylmethyl 6β-allylpenicillanate used in this preparation is prepared by the method described by Hanessian and Alpegiani *Tetrahedron Letters* Vol.27, pp 4857–4860 (1986). This procedure uses the method described in Example 1. From 300 mg(0.683mmol) of 4-Thia- 1-azabicyclo [3.2.0]heptane-2-carboxylic acid, 3,3-dimethyl- 7-oxo-6-(2-propenyl)diphenylmethylester, 4,4-dioxide, [2S-(2α,5α,6β)]-, and 127.4 mg(0.751 mmol) of N-hydroxytolyl 4-carboximidoyl chloride prepared as described by Kou-Chang Lui et al, *J. Org. Chem.* 45, pp 3916–3918(1980), 500 mg of a crude mixture of the two diastereomers is obtained. Flash chromatography using an elution gradient of 5 to 30% ethyl acetate in hexanes affords a separation of the two diastereomers. Compound (A) is obtained as a white solid, m.p. 187°–188°, 42 mg(10.7%). Compound (B) is obtained as a white solid, 82 mg (21%).

Compound A:

Calc'd. for $C_{32}H_{32}N_2O_6S$, MW 572.7): C, 67.11; H,5.63; N,4.89; S,5.60.

9

Found: C, 66.87; H,5.63; N, 4.80; S,5.71.

IR (KBr): 1757 cm$^{-1}$; 1793 cm$^{-1}$ MS: FAB, 573 (M+H)$^+$ $^1$HNMR (CDCl$_3$) δ: 1.09 (s,3H); 1.55 (s,3H); 2.37 (s,3H); 2.44 (m, 2H); 3.07 (m, 1H); 3.45 (m, 1H); 4.10 (m, 1H); 4.53 (s, 1H); 4.63 (d, 1H); 4.88 (m, 1H); 6.98 (s, 1H); 7.20(d,2H); 7.36(m, 10H); 7.55 (d, 2H).

Compound B:

IR(KBr): 1757 cm$^{-1}$; 1795 cm$^{-1}$. MS: FAB, 573 (M+H)$^+$.

$^1$H NMR (CDCl$_3$) δ:1.12 (s, 3H); 1.56(s,3H); 2,20(m, 1H); 2.38 (s, 3H); 2.70 (m, 1H); 3.18 (dd, 1H); 3.51 (m, 1H); 4.15 (m, 1H); 4.53 (s, 1H); 4.67 (d, 1H); 4.85 (m, 1H); 6.97 (s, 1H); 7.21 (d, 2H); 7.35(m, 10H); 7.55(d,2H).

EXAMPLE 4

4-Thia-1-azabicyclo[3.2.0]heptane-2-carboxylic acid, 6-[ [4,5-dihydro-3-(4-methylphenyl)-5-isoxazolyl]-methyl]-3,3-dimethyl-7-oxo-, sodium salt, 4,4-dioxide, [2R-[2α,5α,6β(R*)]]-

A mixture of 176 mg(0.307mmol) of 4-thia-1-azabicyclo [3.2.0]heptane-2-carboxylic acid, 6-[ [4,5-dihydro-3-(4-methylphenyl)-5-isoxazolyl]methyl]- 3,3-dimethyl-7-oxo-, diphenylmethyl ester, 4,4-dioxide, [2S- (2α, 5α, 6β) (R*)]-, prepared in Example 3, 38.6 mg (0.460 mmol) of sodium bicarbonate and 75 mg of 10% palladium on carbon in 25 ml of ethyl acetate and 25 ml of water is shaken under 40 lbs/sq. in. of hydrogen for 3.5 h. The mixture is filtered through diatomaceous earth and the liquid layers are separated. The aqueous layer is extracted with ethyl acetate and stripped of solvent under reduced pressure. The residual solid is dissolved in 2 ml of water and chromatographed on reverse phase preparative plates to give 69 mg (52%) of white solid product.

MS: FAB, 429(M+Na)$^+$.

$^1$H NMR(D$_2$O)δ: 1.29(s,3H); 1.38(s,3H); 1.93 (d, 1H); 2.16 ( s, 3H); 2.35 (q, 1H); 2.91 (dd, 1H); 3.35 (dd, 1H); 4.03 (m, 1H); 4.07 (m, 1H); 4.70 (m, 1H); 4.85 (m, 1H); 7.07 (d, 2H); 7.33 (d, 2H).

EXAMPLE 5

4-Thia-1-azabicyclo[3.2.0.]heptane-2-carboxylic acid, 6-[ [4,5-dihydro-3-(4-methylphenyl)-5-isoxazolyl]methyl]-3,3-dimethyl-7-oxo-, sodium salt, 4,4-dioxide, [2R-[2α,5α,6β(S*)]]-

The method employed in Example 4 is used. From a mixture of 63 mg (0.110 mmol) of 4-Thia-1-azabicyclo[ 3.2.0.]heptane-2-carboxylic acid, 6-[[4,5-dihydro- 3-(4-methylphenyl)-5-isoxazolyl]methyl]-3,3-dimethyl- 7-oxo-, diphenylmethyl ester, 4,4-dioxide, [2S-( 2α,5α,6β) (S*)]-, prepared in Example 3, 9.2 mg (0.110 mmol) of sodium bicarbonate and 38 mg of 10% palladium on carbon in 25 ml of ethyl acetate and 25 ml of water is obtained 38.7 mg(82%) of white solid product giving one spot on a reverse phase thin layer plate developed with 20% ethanol in water. MS: FAB, 429 (M+Na)$^+$.

$^1$H NMR(D$_2$O) δ: 1.20(s,3H); 1.32(s,3H); 1.82(m, 1H); 2.02 (s, 3H); 2.35 (m, 1H); 2.80 (dd, 1H); 3.10 (dd, 1H); 3.90 (m, 1H); 4.02 (s, 1H); 4.74 (m, 2H); 6.90 (d, 2H); 7.18 (d, 2H).

EXAMPLE 6

4-Thia-1-azabicyclo[3.2.0.]heptane-2-carboxylic acid, 6-bromo-6-(1-hydroxy-2-propenyl)-3,3-dimethyl-7-oxo-, diphenylmethyl ester, 4,4-dioxide, [2S-[2α,5α]-

The dibromo carboxylic acid used in the preparation of starting material is prepared as described by Volkmann et al, J. Org. Chem. 47, 33–44 1982). The benzhydryl ester is prepared as described by Just et al, J. Org. Chem. 52 36–59(1987).

Employing the method described by Foulds et al, J. Chem, Sec. Perkin Trans, I, 963–968(1985), 1.18 g of crude product is obtained from 1.00 g (1.79 mmol) of 4-thia-1-azabicyclo [3.2.0.]heptane-2-carboxylic acid, 6,6-dibromo-3,3-dimethyl-7-oxo-, diphenylmethyl ester, 4,4-dioxide, (2S-cis)-, 0.76 ml (2.27 mmol) of 3.0M methylmagnesium bromide in ethyl ether and 0.38 ml (3.16 mmol) of 97% acrolein. Flash chromatography affords 452 mg (47.2%) of product as a single diastereomer. An analytically pure white solid sample, m.p. 173°–174° C. is obtained by recrystallization from ethyl acetate/hexanes.

Calc'd. for (C$_{24}$H$_{24}$BrNO$_6$S, MW534.44): C,53.94; H,4.53; N,2.62; Br,14.95; S,6.00. Found: C,54.06; H,4.39; N,2.35, Br,14.87; S,5.96.

IR(KBr) 1739 cm$^{-1}$; 1807 cm$^{-1}$. MS:553 (M+NH$_4$)$^+$.

$^1$H NMR(CDCl$_3$) δ: 1.13(s,3H); 1.59(s,3H);2.39(d,1H); 4.62(s,1H); 4.78(s,1H); 5.26(m, 1H); 5.47(dd, 1H); 5.61 (dd, 1H); 5.87 (m, 1H); 6.70 (s, 1H); 7.37 (m, 10H).

EXAMPLE 7

4-Thia-1-azabicyclo[3.2.0]heptane-2-carboxylic acid, 6-( 1-hydroxy-2-propenyl)-3,3-dimethyl-7-oxo-, diphenylmethyl ester, 4,4-dioxide, [2S-[2α, 5α, 6β(R* or S*,)]]-

A mixture of 3.11 g (5.82 mmol) of 4-thia-1-azabicyclo[ 3.2.0]heptane-2-carboxylic acid, 6-bromo-6(1-hydroxy-2-propenyl)-3,3-dimethyl-7-oxo-, diphenylmethyl ester, 4,4-dioxide, [2S-(2α, 5α)]- prepared in Example 6, and 1.72 ml (6.4 mmol) of tributyltin hydride is stirred under argon, in an oil bath at 90°, for 2 hours. The mixture is stripped of solvent under reduced pressure. The residual oil obtained is chromatographed and gives 1.60 g (60.4%) of product as a single diastereomer. An analytically pure, white solid sample melts at 141°–143° C. is obtained.

Calc'd. for (C$_{24}$H$_{25}$NO$_6$S, MW 455.5): C, 63.28; H,5.53; N,3.07; S,7.04. Found: C,62.87; H,5.62; N,2.92; S,6.89.

$^1$H NMR (CDCl$_3$) δ: 1.15(s, 3H); 1.55 (s, 3H); 2.52 (d, 1H); 3.85 (dd, 1H); 4.58(s,1H); 4.60(d,1H); 5.25(m, 1H); 5.35 (dd, 1H); 5.50 (dd, 1H); 5.85 (m, 1H); 6.98 (s, 1H); 7.35 (m, 10H).

EXAMPLE 8

4-Thia-1-azabicyclo[3.2.0]heptane-2-carboxylic acid, 6-[ 1-(acetyloxy)-2-propenyl]-3,3-dimethyl-7-oxo, diphenylmethyl ester, 4,4-dioxide, [2S-[2α,5α,6β(R* or S*)]]-

A solution of 200 mg (0.439 mmol) of 4-Thia-1-azabicyclo[ 3.2.0]heptane-2-carboxylic acid, 6-[1-(acetyloxy)- 2-propenyl]-3,3-dimethyl-7-oxo, diphenyl methyl ester, 4,4- dioxide, [2S-[2α, 5α, 6β(R* or S*)]]- prepared in Example 7, 135 mg (1.32) mmol) acetic anhydride, 105 mg(1.32 mmol) of pyridine and 2.5 mg of 4-dimethylamino pyridine in 3 ml of tetrahydrofuran is stirred at room temperature under argon for 16.5 hours. Then, 10 ml of water are added to the reaction mixture and it is extracted with three 10 ml portions of chloroform. The combined extracts are washed with three 10 ml portions of water and dried over anhydrous sodium sulfate and magnesium sulfate. Evaporation gives 212 mg (97%) of white solid product as a single diastereomer.

Calc'd. for ($C_{26}H_{27}NO_7S$, MW 497.5): C,62.76; H,5.47; N,2.82; S,6.44. Found: C,63.05; H,5.73; N,2.61; S.6.25

IR (KBr) 1749 cm$^{-1}$, 1801 cm$^{-1}$.

$^1$H NMR(CDCl$_3$) δ: 1.09(s,3H); 1.57 (s, 3H); 2.10 (s, 3H); 4.05 (dd, 1H); 4.57 (s, 1H); 4.58 (d, 1H); 5.40 (dd, 1H); 5.57 (dd, 1H); 5.82 (m, 1H); 6.28 (m, 1H); 6.98 (s, 1H); 7.34 (m, 10H).

EXAMPLE 9

4-Thia-1-azabicyclo[3,2.0]heptane-2-carboxylic acid, 6-[(acetyloxy)[4,5-dihydro-3(4-methylphenyl)-5-isoxazolyl] methyl]-3,3-dimethyl-7-oxo-, diphenylmethylester, 4,4-dioxide, [2S-(2α,5α,6β(R* or S*)]]-

The title compound is prepared by the method described in Example 1. From 1.12 g (2.25 mmol) of 4-thia- 1-azabicyclo[3.2.0.]heptane-2-carboxylic acid, 6-[1-(acetyloxy)- 2 -propenyl]-3,3-dimethyl-7-oxo-, diphenyl methyl ester, 4,4-dioxide, [2S-[2α,5α, 6β(R* or S*)]]- and 457.9 mg(2.70 mmol) of N-hydroxytolyl 4-carboximidoyl chloride is obtained, after flash chromatography, 531 mg (37.4%) of product as a single diastereomer. An analytically pure, colorless sample melting at 96°–100° C. is obtained.

Calc'd. for ($C_{34}H_{34}N_2O_8S$, MW630.71): C, 64.75; H,5.43; N,4.44; S,5.08. Found: C, 64.30; H,5.64; N,4.35; S,4.82.

IR(KBr): 1752 cm$^{-1}$; 1802 cm$^{-1}$.

$^1$H NMR(CDCl$_3$) δ: 1.14(s,3H); 1.59(s,3H); 2.02(s,3H); 2.38(s,3H); 3.15(dd,1); 3.45(dd, 1H); 4.30(q,1H); 4.58(s, 1H); 4.75(d, 1H); 4.88(m, 1H); 6.24(dd, 1H); 6.98(s,1H); 7.21(d,2H); 7.34(m, 10H);7.53(d,2H).

EXAMPLE 10

4-Thia-1-azabicyclo[3.2,0]heptane-2-carboxylic acid, 6-[(acetyloxy)[4,5-dihydro-3-(4-methylphenyl)-5-isoxazolyl] methyl]-3,3-dimethyl-7-oxo-, sodium salt, 4,4-dioxide, [2S-(2α, 5α, 6β)]-

The title compound is prepared by the method described in Example 4. From a mixture of 139 mg(0.220 mmol) of 4-thia-1-azabicyclo[3.2.0]heptane-2-carboxylic acid, 6-[(acetyloxy)[4,5-dihydro-3-(4-methylphenyl) -5-isoxazolyl] methyl ] -3,3 -dimethyl -7 -oxo-, diphenylmethyl ester, 4,4-dioxide, [2S-(2α, 5α, 6β)]- prepared in Example 9, 22.2 mg(0.265 mmol) of sodium bicarbonate and 50 mg of 10% palladium on carbon in 25 ml of ethyl acetate and 25 ml of water is obtained 7 mg(6.5%) of product after reverse phase preparative plate chromatography.

$^1$H NMR(D$_2$O) δ: 1.28(S,3H); 1.43(s,3H); 1.94(s,3H); 2.23 (s,3H); 3.30(dd,1H); 3.53 (dd, 1H); 4.13 (s,1H); 4.20(dd,1H); 4.80(s,1H); 4.90(m, 1H); 6.01(dd,1H); 7.18(d, 2H); 7.45(d,2H).

EXAMPLE 11

Diphenylmethyl[2S-(2α,5α,6β)]-6-[(3-ethyl-4,5-dihydro-5-isoxazolyl)methyl] -3,3-dimethyl-7-oxo-4-thia-1-azabicyclo[ 3,2,0]heptane-2-carboxylate 4,4 -dioxide.

The title compound is prepared by the method of Mukaiyama et al, *J. Am. Chem. Soc.* (1960) 82, 5339–5345. A mixture of 630 mg (1.44 mmol) of 4-thia-1-azabicyclo[ 3.2.0]heptane-2-carboxylic acid, 3,3-dimethyl- 7-oxo-6-(2-propenyl)-, diphenylmethyl ester, 4,4-dioxide, [2S-(2α, 5α, 6β)]- (See Example 3 for preparation), 357 mg(3 mmol) of phenylisocyanate, 267 mg(3 mmol) of 1-nitropropane and three drops of triethylamine in 15 ml of benzene is stirred under argon for 2 days. The solvent is removed under reduced pressure and the residue obtained is silica gel flash chromatographed (eluted with 40% EtOAc/Hex.) to give 88 mg (12%) of product as a single diastereomer.

$^1$H NMR(CDCl$_3$)δ: 1.15(t,3H); 1.10(s,3H); 1.55(s,3H); 2.33 (m, 4H); 2.62 (dd, 1H); 3.10 (dd, 1H); 4.05 (m, 1H); 4.52(s,1H); 4.63(d, 1H); 4.70(m, 1H); 6.98(s,1H); 7.30 (m, 10H).

EXAMPLE 12

4-Thia-1-azabicyclo[3.2.0]heptane-2-carboxylic acid, 6-(3-ethyl-4,5-dihydro-5-isoxazolyl)-3,3-dimethyl-7-oxo-, 4,4-dioxide, sodium salt, [5R-[5α,6β(R* or S*)]]-, single stereoisomer To a mixture of 88 mg (0.172 mmol) of diphenylmethyl [2S-(2α, 5α, 6β)]-6-[(3-ethyl-4,5-dihydro-5-isoxazolyl)methyl] -3,3-dimethyl-7-oxo-4-thia-1-azabicyclo[ 3.2.0]heptane-2-carboxylate 4,4 dioxide prepared in Example 11, 1.38 ml of anisole and 0.5 ml of methylene chloride is added, under argon with stirring, 58.9 mg(0.441 mmol) of sublimed aluminum trichloride at −60° C. The reaction mixture is stirred for 45 minutes at −60° C. and is treated with 5.2 ml of a 5% sodium bicarbonate solution. The mixture is shaken with 10 ml ethyl acetate and 10 ml of water and the layers are separated. The organic layer is washed with 10 ml of water. The combined aqueous layer is washed with two 10 ml portions of ethyl acetate. The aqueous layer is concentrated to a small volume under reduced pressure and is chromatographed on reverse phase preparative plates (Analtech) (500 microns) and developed with 20% ethanol in water. The bands between Rf 0.4 and 0.7 are scraped and collected and are extracted with 20% water in acetonitrile. The aqueous solution, obtained after removal of acetonitrile under reduced pressure, is washed with hexanes and is lyophilized to give 12 mg(19%) of product as a single diastereomer, one spot by reverse phase, TLC Rf 0.45.

$^1$H NMR(D$_2$O) δ: 1.2(t,3H); 1.3(s,3H); 1.5(s,3H); 2.3(m, 4H); 2.6(dd, 1H); 3.2(m, 1H); 4.1(m, 1H); 4.6(m,3H).

EXAMPLE 13

4-Thia-1-azabicyclo[3,2.0]heptane-2-carboxylic acid, 6-[[4,5-dihydro-3-(3-thienyl)-5-isoxazolyl] methyl]-3,3-dimethyl-7-oxo-, diphenylmethylester, 4,4-dioxide, [2S-[2(2α,5α,6β(S* or R*)]]-

The procedure employed is described in Example 1. From 1.0 g (2.275 mmol) of 4-thia-1-azabicyclo-[ 3.2.0]heptane-2-carboxylic acid, 3,3-dimethyl-7-oxo-6-( 2-propenyl)-, diphenylmethyl ester, 4,4-dioxide, [2S-( 2α,5α,6β)]- (See Example 1) and 459.6 mg (2.844 mmol) of N-hydroxy-3-thiophenecarboximidoyl chloride prepared by the method described by Kou-Chang Liu et al, *J. Org. Chem.* 45, 3916–3918(1980) and 0.4 ml (2.8 mmol) of triethylamine in 10 ml of methylene chloride is obtained 94 mg (5.9%) of the less polar white solid diastereomer (m.p. 70°–72° C.) compound A and 14 mg (1.1%) of the more polar pale yellow oil diastereomer, compound B. In addition to this, 447 mg (34.8%) of a mixture of both A and B after flash chromatography(eluant, 40% ethyl acetate/hexanes) is isolated.

Compound A:

$^1$H NMR(CDCl$_3$)δ: 1.15(s,3H); 1.55(s,3H); 2.20(m, 1H); 2.70 (m, 1H); 3.18 (dd, 1H); 3.50 (dd, 1H); 4.12 (m, 1H); 4.55 (s, 1H); 4.60(d, 1H); 4.82(m, 1H); 7.00(s,1H); 7.35 (m, 11H); 7.50 (m, 2H).

Compound B:

$^1$HNMR(CDCl$_3$)δ: 1.10(S,3H); 1.55(s,3H); 1.63(m, 1H); 2.43 (m, 1H); 3.05 (dd, 1H); 3.48 (dd, 1H); 4.15 (m, 1H); 4.53(s,1H); 4.65(d, 1H); 4–4.87(m, 1H); 7.00(s,1H); 7.35 (m, 11H); 7.50 (m, 2H).

EXAMPLE 14

4-Thia-1-azabicyclo[3.2.0.]heptane-2-carboxylic acid, 6-[[4,5-dihydro-3-(3-thienyl)-5-isoxazolyl] methyl]-3,3-dimethyl-7-oxo-, 4,4-dioxide, sodium salt, [2S-[2α, 5α, 6β(R* or S*)]]-

The method described in Example 12 is used in preparing the title compound. From 119 mg of (0.211 mmol) 4-thia-1-azabicyclo[3.2.0]heptane-2-carboxylic acid, 6-[[4,5-dihydro-3-(3-thienyl)-5-isoxazolyl]methyl]- 3,3-dimethyl-7-oxo-, diphenylmethyl ester, 4,4-dioxide-[ 2S-[2α,5α,6β(S* or R*)]]-, 72 mg(0.54 mmol) of sublimed aluminum trichloride, 1.69 ml of anisole and 0.6 ml of methylene chloride is obtained 56 mg(63%) of pale yellow solid product as a single diastereomer after preparative plate reverse phase chromatography. The plates are developed with 10% ethanol in water.

MS: FAB, 421 ( M+H )$^+$.

$^1$H NMR (D$_2$O) δ:1.04 (s, 3H); 1.17 (s, 3H); 1.70 (m, 1H); 2.25 (m, 1H); 2.80 (dd, 1H); 3.10 (dd, 1H); 3.73 (m, 1H); 3.85 (s, 1H); 4.50 (m, 1H); 4.58 (d, 1H); 6.98 (d, 1H); 7.10(s,1H); 7.25(d, 1H).

EXAMPLE 15

4-Thia-1-azabicyclo[3.2.0]heptane-2-carboxylic acid, 6-[(3-bromo-4,5-dihydro-5-isoxazolyl)methyl]-3,3-dimethyl-7-oxo-, diphenylmethyl ester, 4,4-dioxide, [2S-2α,5α,6β(R* or S*)]]-

The method described in Example 1 is used in preparing the title compound. From 1.0 g(2,275 mmol) of 4-thia-1-azabicyclo-[3.2.0]heptane-2-carboxylic acid, 3,3-dimethyl-7-oxo-6-(2-propenyl)-diphenylmethyl ester, 4,4-dioxide, [2S-(2α,5α, 6β)]- of N-hydroxycarbonimidic dibromide, prepared by D. M. Vyas et al, *Tetrahedron Letters* 25, 487–490(1984) and 1.27 ml (9.1 mmol) of triethylamine in 12 ml of methylene chloride is obtained, after flash chromatography (silica gel; eluant, 30% ethyl acetate/hexanes), 136 mg(10.6%) of product as a colorless oil.

MS: 580 (M+NH$_4$)$^+$.

$^1$H NMR(CDCl$_3$)δ: 1.10(s,3H); 1.55(s,3H); 2.22(m, 1H); 2.68 (m, 1H); 3.05 (dd, 1H); 3.40 (dd, 1H); 4.10 (m, 1H); 4.45 (s, 1H); 4.65(d, 1H); 4.80(m, 1H); 7:00(s,1H); 7.35 (m, 10H).

EXAMPLE 16

4-Thia-1-azabicyclo[3.2.0]heptane-2-carboxylic acid, 6-[(3-bromo-4,5-dihydro-5-isoxazolyl)methyl]-3,3-dimethyl-7-oxo-, 4,4-dioxide, sodium salt, [2S-[2α,5α,6β(R* or S*)]]-

The title compound is prepared by the method described in Example 12. From 136 mg (0.242 mmol) of 4-thia-1-azabicyclo[3.2.0]heptane-2-carboxylic acid, 6-[(3-bromo-4,5-dihydro-5-isoxazolyl)methyl]-3,3-dimethyl-7-oxo-, diphenylmethyl ester, 4,4-dioxide, [2S-[2α,5α,6β(R* or S*)]]-, 82.6 mg (0.62 mmol) of sublimed aluminum trichloride, 1.94 ml of anisole and 0.7 ml of methylene chloride is obtained the crude product. Chromatography on reverse phase preparative plates developed with 10% alcohol in water gives 9 mg(9%) of an off-white solid product (one spot by TLC and as a single diastereomer).

$^1$H NMR(D$_2$O)δ: 1.20(s,3H); 1.32(s,3H); 2.20(m, 1H); 2.45 (m, 1H); 2.80 (dd, 1H); 3.20 (dd, 1H); 3.60 (m, 1H); 3.80 (m, 1H); 4:00 (d, 1H); 4.90 (d, 1H).

BIOLOGICAL ACTIVITY

Pathogenic microorganisms produce β-lactamase enzymes which, in turn inactivate conventional β-lactam antibiotics such as penicillins and cephalosporins. The use of a β-lactamase inhibitor in combination with a β-lactam antibiotic potentiates the effectiveness of the requisite antibiotic against the resistant or partly resistant micro-organism. This principle of potentiation by β-lactamase inhibitors is discussed by H. C. Neu in "Antibiotic Inhibitors of Bacterial Cell Wall Biosynthesis", D. J. Tipper ed. Pergamon Press, 1987, pp. 241–259.

While the 6-[(isoxazolinyl)methyl penicillanic acid 1,1-dioxide compounds of the invention exhibit broad spectrum inhibitory activity against β lactamases of different functional groups, the inhibitory activity again the Group 3 metallo-β-lactamases is of particular interest.

The β-lactamase enzymes may be grouped either according to structural similarities, or according to biochemical function with respect to their ability to hydrolyze (or destroy the activity of) certain β-lactam antibiotics. β-lactamase enzymes of Groups 1 and 2e, also known as cephalosporinases (cephases)hydrolyze predominantly cephalosporins and utilize the amino acid serine at their active site. β-lactamase enzymes of Groups 2a and 4, also serine-based enzymes, exhibit greater specificity for penicillins, and are called penicillinases (penases). The serine enzymes of Groups 2b, 2b', 2c, and 2d can hydrolyze both penicillins and cephalosporins and are known as broad spectrum β-lactamases. Group 3 β-lactamases are enzymes that can be inhibited by metal chelators and utilize a metal ion (commonly zinc) as the β-lactam-hydrolyzing functionality. Enzymes of Group 3 can efficiently hydrolyze penicillin, cephalosporin, and carbapenem classes of antibiotics. Furthermore, none of the marketed β-lactamase inhibitors (clavulanic acid, sulbactam or tazobactam) is clinically effective against those pathogens that produce metallo β-lactamases. Group 3 hydrolyzing enzymes cause the strongest resistance to currently used β-lactam antibiotics or β-lactam/β-lactamase inhibitor combinations. For a more detailed explanation of the classification of β-lactamase enzymes see K. Bush in "Antibiotic Agents and Chemotherapy", Vol. 33, 1989, pages 259–276. Representative 6-[ (isoxazolinyl)methyl]penicillanic acid 1,1-dioxide compounds according to the present invention were tested in a microbiological assay in combination with the penicillin antibiotic piperacillin. The enhanced combined synergistic antibacterial activity is representative of the β-lactamase inhibitory properties of the 6-[(isoxazolinyl)methyl]penicillanic acid 1,1-dioxides I of the present invention. In these tests minimum inhibitory concentrations (MICs) are determined in broth using serial two-fold dilutions with a 1:1 ratio of piperacillin to inhibitor. (N. A. Kuck, N. V. Jacobus, P. J. Petersen, W. J. Weiss and R. T. Testa, "Antibiotic Agents and Chemotherapy", Vol. 33, 1989, pages 1964–1969). The results are in Table I.

TABLE I

Microbiological Testing of Inhibitors
Minimum Inhibitory Concentration
(μg/ml) of Piperacillin*

| ORGANISM | PIPERA-CILLIN | PIPERA-CILLIN + EXAMPLE 10 | PIPERA-CILLIN + EXAMPLE 4 |
|---|---|---|---|
| E. coli 300 | 1 | 1 | 1 |
| E. coli 300 + P99 (cephase) | 16 | 4 | 1 |
| E. coli 300 + CcrA (metalloenzyme) | 4 | 1 | 1 |
| E. cloacae + P99 | 128 | 128 | 16 |
| E. coli + TEM-1 | >1024 | 256 | 256 |

*Inhibitors were tested at a 1:1 ratio with piperacillin.

Referring to Table I, piperacillin exhibits decreased microbiological activity (increased MICs) in E. coli strains that had β-lactamases introduced into them. Example 10 when added to piperacillin lowers the MICs of piperacillin for all the E. coli strains containing β-lactamases. The product of Example 4, when added to piperacillin lowers the MICs for all the β-lactamases-producing strains and shows more potent in vitro activity against the P99 cephase than the product of Example 10.

Representative compounds of the present invention are also tested to determine inhibition of an isolated metallo enzyme Group 3, the β-lactamase Tal 3636 CcrA. $IC_{50}$ values are obtained using a robotic assay in which nitrocefin at 100 μg/ml is used as substrate. In the CI assay, enzyme is added last to a mixture of inhibitor and buffer. In the TDI assay, nitrocefin is added last to a mixture of enzyme and inhibitor that had been incubating for approximately 7 minutes. The sulfone was diluted either into 0.05M phosphate buffer, pH 7.0, or 0.010M HEPES, pH 7.4 The results are shown in Table II.

TABLE II

| EXAM-PLE # | CI $IC_{50}$ (μM) | | TDI | |
|---|---|---|---|---|
| | PHOSPHATE | HEPES | PHOSPHATE | HEPES |
| 5 | 68 | 27.0 | 6.9 | 2.0 |
| 4 | 16 | 9.7 | 2.0 | 1.3 |
| 10 | 210 | 100.0 | 3.2 | 3.9 |

TABLE II-continued

| EXAM-PLE # | CI $IC_{50}$ (μM) | | TDI | |
|---|---|---|---|---|
| | PHOSPHATE | HEPES | PHOSPHATE | HEPES |
| 12 | >250 | >250.0 | 120.0 | 77.0 |
| 16 | 48 | 18.0 | 6.0 | 2.4 |
| 14 | 33 | 48.0 | 9.6 | 3.5 |

Referring to Table II, the results show a time-dependent inhibition associated with all the inhibitors. Selection of HEPES buffer in place of phosphate buffer caused enhanced activity of most inhibitors.

To test for long term inactivation of the metallo-β-lactamase, the inhibitors are mixed with enzyme and incubated overnight. Enzyme activity is tested for at periodic intervals by diluting the enzyme-inhibitor mixture into nitrocefin and comparing the enzymatic activity against that of an enzyme incubated only in assay broth. After 0.7 minutes the metallo-β-lactamase has 45% the control activity when in the presence of 8 μM of the compound of Example 10 and 44% the control activity when mixed with 8μM of the compound of Example 4. However, after overnight incubation, 71% of the metalloenzyme activity is recovered in the presence of the compound of Example 4 whereas: the compound of Example 10 causes >99% of the enzyme activity to be lost.

The β-lactamase inhibitory action against the metalloenzymes (Group 3) of the compounds in the present invention therefore comprise an important contribution to antimicrobial therapy against pathogens which generate such metalloenzymes.

Representative compounds were also tested against the commercially available inhibitors clavulanic acid, sulbactam, tazobactam to determine inhibition of the CccA (metallo), PC1 (penase) TEM-2 (Bd spectrum) and P99 (cephase) β-lactamase enzymes. $IC_{50}$ values are 20 determined spectrophotometrically using a 10 minute preincubation of enzyme with inhibitor at 25° C. before addition of nitrocefin as substrate (100 βg/ml). The results are shown in Table III.

TABLE III

| | $IC_{50}$ (μM) | | | |
|---|---|---|---|---|
| | CcrA (Metallo) | PC1 (Penase) | TEM-2 (Bd Spectrum) | P99 (Cephase) |
| Example 4 | 0.65 | 0.72 | 0.70 | 0.0028 |
| Example 10 | 16.0 | 8.0 | 1.2 | 2.4 |
| Clavulanic acid | >500 | 0.03[a] | 0.13[a] | >100[a] |
| Sulbactam | >500 | 0.080 | 1.6[a] | 5.6 |
| Tazobactam | 320 | 0.032 | 0.011 | 0.009 |

As shown in Table III, the compound of Example 4 is a very potent inhibitor of the P99 Group 1 cephalosporinase. The PC1 Group 2a penicillinase, 2b broad spectrum β-lactamase and Group 3 metallo-β-lactamases are inhibited about equally by the compound of Example 4. Both compounds of the present invention are better inhibitors of the metallo enzyme than the commercially available inhibitors, clavulanic acid or sulbactam. Inhibition by compounds are superior to any of the previously described β-lactam inhibitors for this enzyme (Y. Yang, B. A. Rasmussen, and K. Bush, in "Antibiotic Agents and Chemotherapy", Vol. 36, 1992, pages 1155–1157).

When the compounds are employed for the above utility, they may be combined with one or more pharmaceutically acceptable carriers, for example, solvents, diluents and the like, and may be administered parenterally in the form of sterile injectable solutions or suspensions containing from about 0.05 to 5% suspending agent in an isotonic medium. such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 2 to about 100 mg/kg of animal body weight, preferably given in divided doses two to four times a day. For most large mammals, the total daily dosage is from about 100 to about 750 mg, preferably from about 100 to 500 mg. Dosage forms suitable for internal use comprised from about 100 to 750 mg of the active compound in intimate admixture with a liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered by intravenous, intramuscular, or subcutaneous routes. Liquid carriers include sterile water, polyethylene glycols, non-ionic surfacrants and edible oils such as corn, peanut and sesame oils, as are appropriate to the nature of the active ingredient and the particular form of administration desired. Adjuvants customarily employed in the preparation of pharmaceutical compositions may be advantageously included, such as coloring agents, preserving agents, and antioxidants, for example, vitamin E, ascorbic acid, BHT and BHA.

These active compounds may also be administered parenterally or intraperitoneally. Solutions or suspensions for these active compounds can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injection use include sterile aqueous solution for dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersions medium containing, for example, water, ethanol, polyol (e.g. glycerol, propylene glycol and liquid polyethylene glycol), suitable mixtures thereof, and vegetable oils.

We claim:

1. A method of producing a compound of the formula:

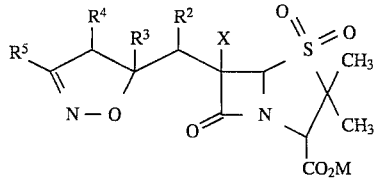

wherein:

M is H, Na, Li or K;

X is OH or Br;

$R^2$ is H; $C_1$–$C_4$ alkyl; $C_1$–$C_4$ substituted alkyl with substitution selected from F, Cl, Br, I, OH and $NH_2$; acetate; benzoate; F; Cl; Br or I;

$R^3$ is H; $C_1$–$C_4$ alkyl; $C_1$–$C_4$ substituted alkyl with substitution selected from F, Cl, Br, I, OH and $NH_2$; OH; $NH_2$; acetyloxy; benzoate; F, Cl; Br or I;

$R^4$ is H; $C_1$–$C_4$ alkyl; $C_1$–$C_4$ substituted alkyl with substitution selected from F, Cl, Br, I, OH and $NH_2$; acetate; benzoate; F; Cl; Br or I;

$R^5$ is H; $C_1$–$C_4$ alkyl; $C_1$–$C_4$ substituted alkyl with substitution selected from F, Cl, Br, I, OH and $NH_2$; 2- or 3-thienyl; F; Cl; Br; I; phenyl; substituted phenyl with substitution selected from $C_1$–$C_4$ alkyl, F, Cl, Br, I, OH and $NH_2$; which comprises reacting a compound of the formula:

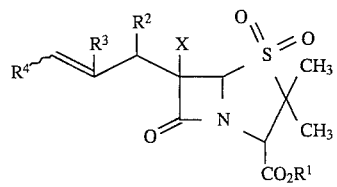

wherein $R^2$, $R^3$, $R^4$ and X are as defined hereinabove and $R^1$ is a carboxylic acid protecting group; with a compound of the formula:

wherein $R^5$ is as defined hereinabove; at a temperature of about –78° C. to about 25° C. for a time of about 0.5 to 5 hours, to obtain a compound of the formula:

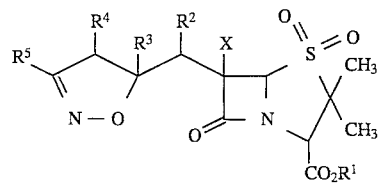

wherein $R^1$, $R^2$, $R^3$, $R^4$, $R^5$, and X are as defined hereinabove; and deprotecting the carboxylic acid group to obtain the desired compound.

2. A method of producing a compound of the formula:

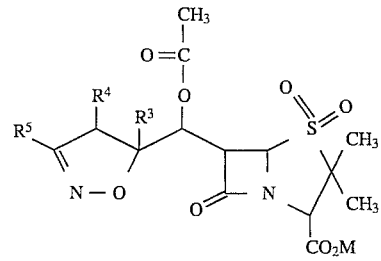

wherein:

M is H, Na, Li or K;

$R^3$ is H; $C_1$–$C_4$ alkyl; $C_1$–$C_4$ substituted alkyl with substitution selected from F, Cl, Br, I, OH and $NH_2$; OH; $NH_2$; acetyloxy; benzoate; F, Cl; Br or I;

$R^4$ is H; $C_1$–$C_4$ alkyl; $C_1$–$C_4$ substituted alkyl with substitution selected from F, Cl, Br, I, OH and $NH_2$; acetate; benzoate; F; Cl; Br or I;

$R^5$ is H; $C_1$–$C_4$ alkyl; $C_1$–$C_4$ substituted alkyl with substitution selected from F, Cl, Br, I, OH and $NH_2$; 2- or 3-thienyl; F; Cl; Br; I; phenyl; substituted phenyl with substitution selected from $C_1$–$C_4$ alkyl, F, Cl, Br, I, OH and $NH_2$; which comprises reacting a compound of the formula:

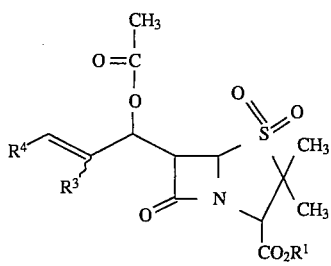

wherein $R^3$ and $R^4$ are as defined hereinabove and $R^1$ is a carboxylic acid protecting group; with a compound of the formula:

$R^5$—C≡$N^+O^-$ wherein $R^5$ is as defined hereinabove; at a temperature of about $-78°$ C. to about $25°$ C. for a time of about 0.5 to 5 hours, to obtain a compound of the formula:

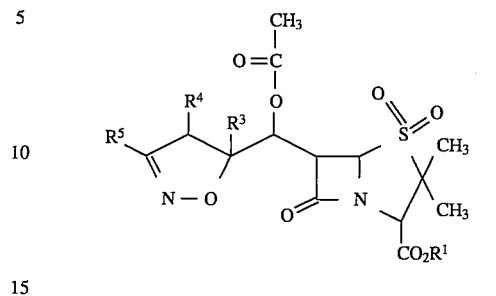

wherein $R^1$, $R^3$, $R^4$, and $R^5$ are as defined hereinabove; and deprotecting the carboxylic acid group to obtain the desired compound.

* * * * *